(12) United States Patent
Streiff et al.

(10) Patent No.: US 10,479,875 B2
(45) Date of Patent: *Nov. 19, 2019

(54) PROCESS FOR THE TREATMENT OF A COMPOSITION COMPRISING THERMOPLASTICS

(71) Applicant: SOLVAY SA, Brussels (BE)

(72) Inventors: Stéphane Streiff, Shanghai (CN); Dominique Balthasart, Brussels (BE); Armin T. Liebens, Shanghai (CN); Gérard Antonini, Paris (FR)

(73) Assignee: SOLVAY SA, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/743,048

(22) PCT Filed: Jul. 13, 2016

(86) PCT No.: PCT/EP2016/066685
§ 371 (c)(1),
(2) Date: Jan. 9, 2018

(87) PCT Pub. No.: WO2017/009389
PCT Pub. Date: Jan. 19, 2017

(65) Prior Publication Data
US 2019/0085147 A1    Mar. 21, 2019

(30) Foreign Application Priority Data

Jul. 14, 2015 (EP) ..................................... 15176693

(51) Int. Cl.
*C07C 4/22* (2006.01)
*C08J 11/12* (2006.01)
*C08J 11/08* (2006.01)

(52) U.S. Cl.
CPC ............... *C08J 11/12* (2013.01); *C07C 4/22* (2013.01); *C08J 11/08* (2013.01); *C08J 2323/06* (2013.01); *C08J 2323/12* (2013.01); *C08J 2325/06* (2013.01)

(58) Field of Classification Search
USPC .................................. 521/47, 50, 59, 63, 64
See application file for complete search history.

(56) References Cited

U.S. PATENT DOCUMENTS 5,569,801 A    10/1996  De Broqueville
2003/0019789 A1    1/2003  Kwak

FOREIGN PATENT DOCUMENTS

EP    1057854 A2    12/2000
FR    2846334 A1    4/2004

*Primary Examiner* — Terressa Boykin

(57) ABSTRACT

The present invention relates to a process for the treatment of a composition comprising thermoplastics comprising introducing the composition into a reactor under reduction of oxygen content of the atmosphere, heating the composition in the presence of a solvent to liquefy the thermoplastics, separating insoluble fractions and recovering the liquefied thermoplastics which process is conducted in one reactor.

12 Claims, 3 Drawing Sheets

PROCESS FOR THE TREATMENT OF A COMPOSITION COMPRISING THERMOPLASTICS

This application is a U.S. national stage entry under 35 U.S.C. § 371 of International Application No. PCT/EP2016/066685 filed Jul. 13, 2016, which claims priority to European application No. 15176693.8—filed on Jul. 14, 2015. The entire contents of these applications are explicitly incorporated herein by this reference.

The present invention relates to a process for the treatment of a composition comprising thermoplastics comprising introducing the composition into a reactor under reduction of oxygen content of the atmosphere, heating the composition in the presence of a solvent to liquefy the thermoplastics, separating solid and gaseous fractions and recovering the liquefied thermoplastics, which process is conducted in one reactor.

Mixed industrial or post-consumer plastics comprising a significant amount of thermoplastics are available from sorting plants as mixed plastic objects of large size contaminated with several impurities. The chemical valorization or recycling of these mixed plastics comprising a significant amount of thermoplastics typically needs a pretreatment step that, optionally including the reduction of the particle size to suitable ranges, comprises a step of separation of detrimental impurities such as wood, paper, glass, undesired plastics, air, water, etc.

Processes for recycling of waste plastics which process comprises a step of melting the waste plastic followed by cracking the plastic melt are known in the art.

WO 01/70906 A1 discloses a method for the continuous preparation of gasoline, kerosene, and diesel oil from waste plastics, comprising the steps of subjecting a melt of the waste plastic to a first catalytic reaction in which the waste plastic melt is dehydrogenated while being decomposed, and subjecting the waste plastic melt to a catalytic cracking. The pretreatment disclosed consists of a crushing and sorting step, a melting step, and an impurity-precipitating step. In a first melting device, the melt is dewatered to have a water content of about 10% or less, followed by elevating the temperature to 150° C. The melt is then introduced into a second melting device to further elevate the temperature to about 340-360° C. The secondly melted waste plastic is then introduced into a further melting tank to remove impurities, for being transferred to a reactor for dehydrogenation and decomposing.

U.S. Pat. No. 5,569,801 relates to a process for the conversion of polymers, in particular plastic wastes, into products of lower molecular weight. This process comprises the steps of placing the polymers in contact with a solvent which has a boiling temperature higher than 180° C. and is composed predominantly of aromatic hydrocarbons, extraction of formed decomposition gases, recovery of the polymer solution, and treatment of this polymer solution by a cracking process, such as thermal or catalytic cracking. In this process the waste polymers are first contacted with a solvent in a mixing device, optionally followed by a separator device. The polymer and the solvent are then, in a further device subjected to heating, before being transferred to a suitable cracking reactor.

Using several different devices for the pretreatment of a composition comprising thermoplastics in a cracking process is disadvantageous due to the efforts and costs accompanied by each individual device and reactor which has to be passed during the process. Therefore, there is a need in the art for a simplified more economic process for the pretreatment of a composition comprising thermoplastics, in particular waste plastics.

Surprisingly an advantageous process for the (pre-)treatment of a composition comprising thermoplastics has been found which is more economic and which substantially only requires one reactor for bringing the composition comprising thermoplastic into contact with a solvent, separating solid and/or gaseous fractions and thereby removing impurities, liquefying the thermoplastics and recovering the liquefied thermoplastics.

The present invention therefore relates to a process for the treatment of a composition comprising thermoplastics comprising the steps of a) introducing the composition comprising thermoplastics into a reactor under reduction of oxygen content of the atmosphere, b) heating the composition comprising thermoplastics in the presence of a solvent to obtain liquefaction of a substantial part of the thermoplastics, c) separating solid and/or gaseous fractions at the surface of the mixture and/or the bottom of the reactor, and d) recovering liquefied thermoplastics from the reactor, wherein the process steps a) to c) are conducted in one reactor.

The invention proposes to separate the valuable plastic from a composition comprising thermoplastics, which composition may comprise an amount of impurities, as a solution or melt, possibly diluted by a suitable solvent, such as a hydrocarbon cuts, while separating insoluble fractions, such as gaseous impurities, water and solid impurities by decantation and flotation of insoluble material. By using the pre-treatment process of the invention, a composition comprising thermoplastics, such as a crude plastics or waste plastics, can be used for the cracking process, and a high purity plastic will not be required.

The invention therefore allows for producing valuable chemicals from a composition comprising thermoplastics, preferably waste plastics such as post-consumer waste plastics, off spec plastics, industrial scrap plastic or the like. More particular, the mixture of thermoplastics includes waste plastics or industrial scrap plastics, in particular substantially consists of waste plastics. Thermoplastics, or thermoplastic material, as used herein is as known in the art a plastic material, typically a polymer that becomes pliable or moldable above a specific temperature and solidifies upon cooling. Thermoplastics differ from thermosetting (thermoset) polymers which do not melt upon heating, but typically decompose. Examples of thermoset polymers are polyurethanes, vulcanized rubber, and epoxy resins as well as thermoset polyester resins. Preferred examples of thermoplastics as used according to the invention are polyolefines, such as polypropylene (PP) and polyethylene (PE), polyacrylates, polycarbonates, poly ether sulfones, polystyrene (PS), polyvinyl chloride, thermoplastic polyesters such as polyethylene terephthalate (PET), polytrimethylene terephthalate (PTT), polybutylene terephthalate (PBT) and polybutylene succinate (PBS), or fluorinated polymers like Teflon. More preferred the thermoplastics are polyolefins, thermoplastic polyesters, and polystyrene, in particular polyolefins and polystyrene, more particularly polyolefins, such as polyethylene, including high density polyethylene (HDPE) and low density polyethylene (LDPE) and polypropylene.

The thermoplastics used in the process may include mechanically assembled mixed plastic, glued mixed plastic, multilayered film plastic, multilayered plastic objects, composite plastic, etc.

The thermoplastics used in the process typically comprise other components than polymeric plastic materials, such as additives including fillers, reinforcers, processing aids, plasticizers, pigments, light stabilizers, lubricants, impact modifiers, antistatic agents, ink, antioxidants, etc.

The amount of other components than thermoplastic material in the thermoplastics of the composition of the invention may vary largely. Typically the amount of the other components is less than 60% by weight, preferably less than 40% by weight, more preferably less than 20% by weight, even more preferred less than 10% by weight, in particular less than 5% by weight, e.g. less than 2% by weight, based on the total weight of the composition.

Substantially comprising or substantially consisting of as used herein means at least 80%, preferably at least 90%, more preferably at least 95%, e.g. at least 98%. Percentages given herein are % by weight, based on the total weight of the composition, respectively, if not indicated otherwise, preferably based on the composition on dry and air free basis.

In step a) of the process of the invention the composition comprising thermoplastics is introduced into a reactor. Preferably the thermoplastics are in the form of particles, as known and available in the art, typically from conventional dry treatment including size reduction by grinding or shredding, separation by cycloning, elutriation, or magnetic separation of plastics, such as waste plastics. In a preferred embodiment the process steps a)-d) of the process of the invention are preceded by a step of reduction of the particle size of the thermoplastics in the composition comprising thermoplastics to a suitable particle size. Preferably, the thermoplastics in the form of particles are free-flowing, e.g. a free-flowing granular solid. The particles preferably have an average size in the range of 10-100 mm, more preferably in the range of 10-50 mm. Suitable apparatuses for preparing and obtaining thermoplastics in the form of particles as specified herein are known in the art.

The composition comprising thermoplastics as introduced in step a) preferably has a water content of at most 20% by weight more preferably at most 15% by weight, in particular at most 10% by weight, and preferably at least 1% by weight, more preferably at least 2% by weight, based on the total weights of the composition. Preferably the water content is in the range of 1-20% by weight, in particular in the range of 2-15% by weight. The content of impurities, i.e. non-polymeric and polymeric solids which are not thermoplastics and not thermoset polymers, of the composition comprising thermoplastics is usually between 0.1 and 5% by weight of solids, in particular in between 1 and 3% by weight of solids. The impurities include organic materials and inorganic materials different than polymers, such as stones, soil, inorganic salts, metal, glass and alike. Examples of organic material are paper, food residues, textiles, wood, etc. Examples of inorganic materials are metallic and mineral solids, such as aluminum, iron, copper, steel, stone, calcium carbonate, alumina, $TiO_2$, talc, silicates, glass, etc. In a preferred embodiment, the composition comprising thermoplastics as used in the process of the invention comprises at least 75% by weight of solids, more preferably at least 95% by weight of solids, in particular at least 97% by weight of solids of thermoplastics, wherein preferably the thermoplastics are constituted of one or more polyolefines, polystyrene and thermoplastic polyesters. Preferably, the fraction of polyolefin, polystyrene and thermoplastic polyesters in the composition comprising thermoplastics is at least 50% by weight, more preferably at least 75% by weight, and in particular the thermoplastics in the composition substantially consists of polyolefin, polystyrene and thermoplastic polyesters. Preferably, the composition comprising thermoplastics comprises less than 99.5% by weight of polyolefin, polystyrene and thermoplastic polyesters, more preferably less than 99% by weight. As polyolefines, polypropylene and polyethylene are preferred. As above indicated, weight of solids preferably refers to dry and air free basis. Solids refers to substances which are solid at room temperature (20° C.).

Optionally, the composition comprising thermoplastics comprises minor amounts of less desirable plastics such as PVC, PVDC, PU, ABS, nylon, fluorinated polymers (such as polytetrafluoroethylene) and mixtures thereof. Preferably, the content of these less desirable plastics in the composition comprising thermoplastics is 25% by weight of solids or less. More preferably, the content of the less desirable plastics in the composition comprising thermoplastics is lower than 15% by weight of solids, in particular less than 2% by weight of solids.

Typically, thermoplastics, in particular in the form of particles, as used in pre-treatment processes before being subjected to cracking comprise air, typically in a range between 0.5 and 20 kg/1,000 kg of dry solids. In step a) of the process of the invention the composition comprising thermoplastics, preferred in the form of particles, is introduced into the reactor under reduction of the oxygen content of the atmosphere. Reduction of oxygen used therein means reducing the oxygen content of the atmosphere lower than the typical oxygen content of air, which is about 20.95 vol. % of gas phase (dry basis). The oxygen content of the atmosphere may be reduced by known process steps, such as diluting the atmosphere by a suitable inert gas, purging the solids with a suitable inert gas before introducing into the reactor, applying a vacuum, or reacting the oxygen with a suitable scavenger such as sulfite solution. When a pneumatic transportation is used, which is preferred, as a transportation gas a suitable inert gas may be used. Suitable inert gases are steam, nitrogen, carbon dioxide or combustion gases, steam and combustion gases are preferred. Alternatively, the oxygen content could be reduced by removal of air by application of vacuum in a continuous or a batch process. In this case, when the composition comprising thermoplastics are introduced into the reactor the atmosphere is replaced by reactor atmosphere, whereby the oxygen content of the atmosphere is reduced. Preferably the residual oxygen content in the reactor is reduced to below 10 vol. % of gas phase, more preferably below 5 vol. % of gas phase, e.g. below 2 vol. % of gas phase.

The composition comprising thermoplastics is introduced into the reactor by any suitable means known in the art. Examples of suitable means are screw conveyer, belt conveyer, pneumatic transportation, bucket elevator, or flexiscrew (transitube). Screw conveyer or pneumatic transportation is preferred. Pneumatic transportation is preferably made using the inert gas as defined above. Preferably, by pneumatic transportation using an inert gas and the oxygen content of the atmosphere surrounding the particles is reduced.

Suitable reactors for the process of the invention are known in the art. Typically the chamber of the reactor comprises a number of zones. By zone an area is meant where defined hydrodynamics take place. Preferably the reactor comprises at least two zones, in particular two zones, one comprising suitable means for agitating the content, and a second zone without agitating. In the agitated zone the contents are mixed, while in the second zone the decantation and separation by gravity may take place. The zones may be separated by suitable means, such as a screen and/or baffle. The zones are preferably interconnected.

In step b) of the process of the invention the composition comprising thermoplastics is heated in the presence of a suitable solvent to achieve liquefaction of substantial part of the thermoplastics. Substantial part means preferably at least 50% by weight, more preferably at least 80% by weight, in particular at least 90% by weight, e.g. at least 99% by weight, based on the total content of thermoplastics. As used herein, liquefaction is defined by a drop of viscosity below $10^4$ mPas, preferably below $10^2$ mPas (at the respective temperature). Heating can be conducted by any means known in the art. For instance, heating can be conducted by direct or indirect contact with a heater transfer medium, by mechanical friction, by induction, by radiation, or electrical power. Preferably, heating is conducted by direct or indirect contact with a heat transfer medium, in particular by indirect contact. Examples of indirect contact with heat transfer medium, is in an agitated closed vessel, screw auger, a rotating drum equipped with suitable heat transfer area, etc. Suitable heat transfer media are hot inert gas, steam or heat transfer oils.

The composition comprising thermoplastics is heated in step b) in the presence of a suitable solvent. Preferably, the solvent is a compound or mixture of compounds which are liquid during step b) e.g. before, during and/or after heating to the final temperature in step b). Before heating, e.g. at room temperature (20° C.) the solvent may be liquid or solid. Typical solvents are hydrocarbons, e.g. oil, bio diesel or hydrocarbon cuts and mixtures thereof, which are known and available. The hydrocarbons can be saturated or unsaturated, or a mixture thereof. Saturated hydrocarbons are preferred. Saturation can be determined according to the iodine index. Saturated hydrocarbon as used herein means hydrocarbons having a bromine number of less than 5, preferably at most 2, determined according to ASTM D1159-07 (2012). Hydrocarbon cut is preferred. Hydrocarbon cut is a mixture of hydrocarbons and is e.g. available from pyrolysis of plastics. Gasoline cut available from pyrolysis of plastics is particular preferred. In a preferred embodiment the solvent used in step b) is an aliphatic hydrocarbon, preferably having a boiling point of between 50° C. and 150° C. (at standard conditions, 1 atm). While minor contents of aromatic hydrocarbon in the solvent of e.g. at most 5% by weight are still acceptable in accordance with the present invention, the content of aromatic hydrocarbons preferable is at most 3% by weight, more preferably at most 2% by weight in particular at most 1% by weight, e.g. at most 0.5% by weight. The aliphatic hydrocarbon can be linear or branched, or a mixture of both. The branching can be iso-branching or tertiary-branching (tert- or neo-), iso-branching is preferred, in particular methyl-isobranching. Most preferred, an aliphatic hydrocarbon, or a mixture thereof, having a boiling point between 50° C. and 150° C. is used, such as one or more $C_6$ to $C_8$ aliphatic hydrocarbons, in particular $C_6$ to $C_8$ alkanes. The solvent, preferably the aliphatic hydrocarbon, may comprise minor amounts of oxygen, typically in the form of organic compounds, such as at most 15% by weight, preferably at most 10% by weight of the solvent. The solvent may further comprise minor amounts of water, preferably no more than the amount of water which is soluble in the respective solvent. Minor amounts of ashes are acceptable in the solvent, preferably no more than 1% by weight, more preferably no more than 0.1% by weight of the solvent. Ash content can be measured according to ASTM E1534.

In one embodiment the solvent used in step b) has a melting point of at least 40° C., preferably at least 45° C., and preferably at least 50° C., in particular at least 60° C. Preferred an aliphatic hydrocarbon with such melting point is used. Preferred paraffin aliphatic waxes, i.e. mixtures of aliphatic hydrocarbons, in particular as defined above, are used, which typically melt above 40° C. preferably 45° C. Preferred examples are aliphatic waxes, are $C_{18+}$ ($C_{18}$ or higher) or $C_{30+}$ aliphatic waxes. The solid solvents can be introduced in step b) as such or after melting of the solvents, e.g. in a separate device. Examples of suitable devices are heated tanks, heat exchangers or extruders. Introduction of solid aliphatic waxes without prior melting is preferred.

In one preferred embodiment, the solvent forms an azeotropic mixture with water, which is particular suitable to remove the residual water and the water produced by the reaction of the plastics and/or the impurities or by the decomposition of the plastics and/or the impurities from the composition comprising thermoplastics.

In a preferred embodiment in step b) the composition comprising thermoplastics is heated in the presence of a solvent to a temperature in the range of 150-450° C., preferably in the range of 250-450° C., in particular in the range of above 250° C. to 400° C., e.g. above 250° C. to 350° C. Typically in these temperature ranges a substantial amount of the thermoplastics is liquefied. Substantial amount as used herein means at least 20% by weight, preferably at least 50% by weight, more preferably at least 70% by weight, in particular at least 80% by weight.

The amount of solvent as used in step b) is such that a substantial amount of thermoplastics is liquefied. Typical amounts of solvent are 0.1 kg to 10 kg per kg thermoplastics, preferably in the range of 0.2 to 4 kg solvent per kg thermoplastics, e.g. 0.5 to 3.0 kg solvent per kg thermoplastics.

In step c) of the process of the invention solid and/or gaseous fractions are separated. These fractions both comprise gaseous impurities, which are present or are formed during heating step b), as well as insoluble solids or liquids. Insoluble fractions may be removed from the bottom of the reactor, preferably by continuous extraction, e.g. via a screw device. Examples of screw devices are screw auger, twin screw extruder, Moineau™ pump, Vulcain™ pump, Moineau™ HR pump, and the like. Alternatively, insoluble solid could be removed by gravity batchwise with a device using a combination of valves. Examples of such fractions include the inorganic materials of the composition as defined above, e.g. tin can, scrap iron, dust, etc. Insoluble fractions which are solid or liquid and are lighter than the liquefied thermoplastics can be removed from the surface of the composition in the reactor, which removal preferably is conducted continuously. Typical examples of such fractions are wood, wool, tissue, cardboard or paper. The liquefied thermoplastics of the composition comprising thermoplastics are recovered in step d) from the reactor. Preferably, this is done continuously, e.g. via a suitable pumping device as known in the art. Examples of suitable devices are pumping device, scraper, "blower", extraction screw. Examples of suitable pumping devices are gear pump, gas ejector, vacuum pump Moineau™ pump, Vulcain™ pump, Moineau™ HR pump and the like. Examples of extraction screw are single screw extruder, twins screw extruder, single screw auger, multi screw auger, and the like.

In one embodiment, in step c) gaseous compounds, such as steam and other gases generated by the heating of the thermoplastics, are separated above the surface of the composition. These gases may be condensated and recovered for a separate treatment process. Suitable condensation devices are known in the art, examples are heat exchanger, adsorption, absorption system or a combination thereof, particularly suitable is absorption in an aqueous media; example of aqueous media is water, basic solution such as caustic soda, sodium carbonate, sodium bicarbonate, lime, magnesium carbonate and the like. Example of suitable adsorption system are caustic solid absorbent such as caustic soda pearl, sodium bicarbonate, sodium carbonate, lime, soda lime, magnesia, alumina and the like. The generated gases typically include inorganic and organic gases or mixtures thereof, such as hydrogen halides, e.g. HCl, HBr, HF, carbon oxide/carbon dioxide, sulfur compounds like $H_2S$, COS, $SO_2$, nitrogen compounds like HCN, $NH_3$, NOx, etc. Typically, the gaseous stream is separated by gravity and it may be sent to a scrubber to capture and remove undesirable gases. Preferably, a condenser is introduced before the scrubber.

It has been found in the present invention that when both the oxygen content of the atmosphere surrounding the thermoplastics when introducing these into the reactor is reduced, and a suitable solvent is used for liquefaction of a the thermoplastics, this pre-treatment process can be conducted in one reactor, preferably continuously. That is, process steps a)-c) are preferably conducted continuously, preferably simultaneously, in one reactor. This way, separate devices, e.g. for mixing the thermoplastic with a solvent, for heating, or for separating impurities, respectively can be avoided, which renders the total process more economical. Furthermore, the use of an azeotropic mixture of the solvent with water has been shown to be suitable to remove the water from the composition comprising thermoplastics in order to provide an advantageous liquefied thermoplastic mixture.

The process of the invention is an advantageous pre-treatment of composition comprising thermoplastics in order to be subjected to known recycling processes, such as cracking processes, e.g. for the preparation of further chemicals such as fuels. Therefore, preferably, process steps a)-d) are followed by a step e) of cracking the liquefied thermoplastics, preferably by thermal cracking or catalytic cracking, as e.g. disclosed in WO 01/70906.

It should be noted that the present description is by way of instructional examples, and the concepts presented herein are not limited to use or application with any single treatment method and/or apparatus. Hence, while the details of the innovation described herein are for the convenience of illustration and explanation with respect to exemplary embodiments, the principles disclosed may be applied to other types and applications of waste plastic methods and apparatus without departing from the scope hereof.

Figure 3:
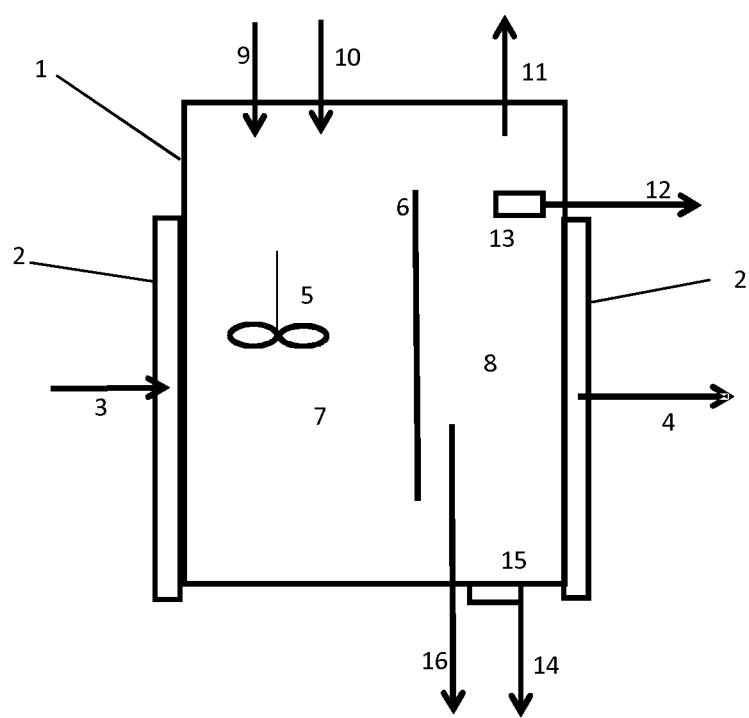
FIG. 3 shows a system for generating melt from mixed waste plastic.

According to the invention, the system for generating melt from mixed waste plastic as shown in FIG. 3 comprises an enclosure 1 equipped with an indirect heating device 2 and 2' where heat transfer medium is introduced through 3 and recovered through 4. The separation device 6 divides the enclosure 1 into two interconnected zones 7 and 8. A mixed zone 7 is equipped with a mixing device 5 and a decantation zone 8. The mixed plastic feed with reduced oxygen content is introduced in the mixed zone 7 by the pipe 9 and the solvent is introduced by the pipe 10. The plastic is mixed with the solvent and heated by the heating devices in the zone 7 and is transferred by gravity to zone 8 where most of the decantation takes place. Gaseous impurities are recovered from the top of the enclosure 1, extracted by the pipe 11 and directed to a further treatment not shown in the FIG. 3. Light insoluble fraction is recovered through the device 13 is evacuated by the pipe 12 and directed to a further treatment. The heavy insoluble fraction is recovered by the device 15, evacuated through the pipe 14 and directed to a further treatment. The liquefied thermoplastics are recovered from the zone 8 through the pipe 16 and directed to a further treatment. The invention is further illustrated by the following examples.

EXAMPLE 1

A 2 liter closed tank is externally heated at a temperature in the range of 150-300° C. The waste plastic composition used has the following composition (in g/kg solids):

| Component | g/kg solids ("dry and air free") |
| --- | --- |
| HDPE | 442 |
| PP | 326 |
| PS | 81 |
| PET | 119 |
| PVC | 4 |
| Foreign materials (1) | 28 |
| Water | 100 |
| Air | 20 |

(1) Metal, dust, stone, wool, cardboard, paper and the like

Said composition comprising the mixture of plastics of which the air has been evacuated by a vacuum pump up to a residual pressure of 10 mbar and replaced by nitrogen is continuously fed into the reactor at the rate of 0.4 kg/h along with 0.92 kg/h of docosane as solvent. The heating is conducted by an external electrical heat jacket. Pressure in the reactor is in the range of 1.1 to 1.5 bar absolute, the residence time of the plastic is approximately 30 min. The tank is divided by a separation screen in two zones, one be mixed with a steering impeller where the incoming load of thermoplastic particles is fed in over-feed within the tank to come in contact with the solvent. In the second zone, which is non-mixed, the melted liquid is decanted, both by sedimentation of the heavy undesired solids and by upwards flotation of light undesired substances. Heavy undesired solids comprised such component as metal, dust, stone or paper. Light undesired substances comprise components as wool or cardboard. Gaseous substances are recovered from the top of the tank, and send to a condenser to condense and recover condensable fraction for a separate treatment process.

The recovered liquefacted thermoplastics from the reactor show a residual impurity content of below 2% by weight and therefore could be excellently used for thermal cracking following process step.

EXAMPLE 2

Figure 1:
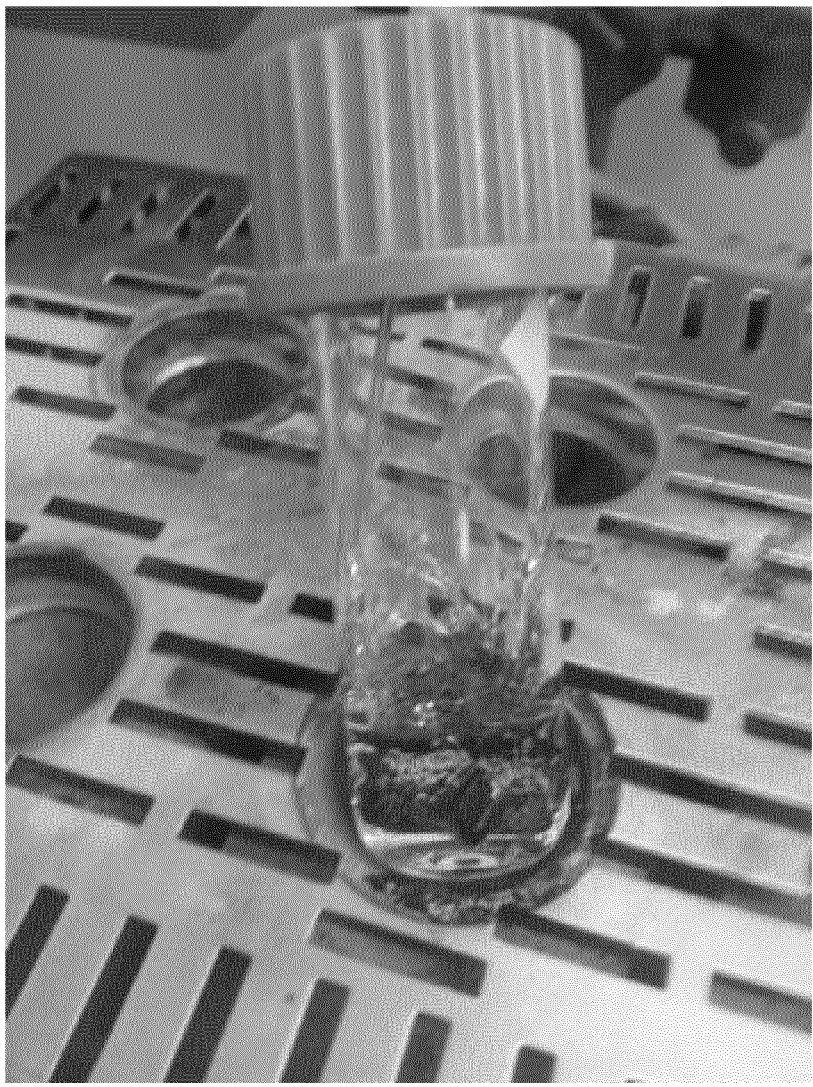
FIG. 1 shows the product of melting at 280° C. a sample of HDPE and PP under $N_2$ atmosphere (replacing air by $N_2$)

A sample of HDPE and PP post-consumer plastic is introduced in a laboratory test tube equipped with a stopper. Air is evacuated by a vacuum pump up to a residual pressure of 10 mbar and replaced by nitrogen. The residual $O_2$ content is estimated to 0.2 to 0.3% volume. The tube is heated externally up to 280° C. The thermoplastic mixture melts and stays clear as seen in FIG. 1.

EXAMPLE 3

Figure 2:
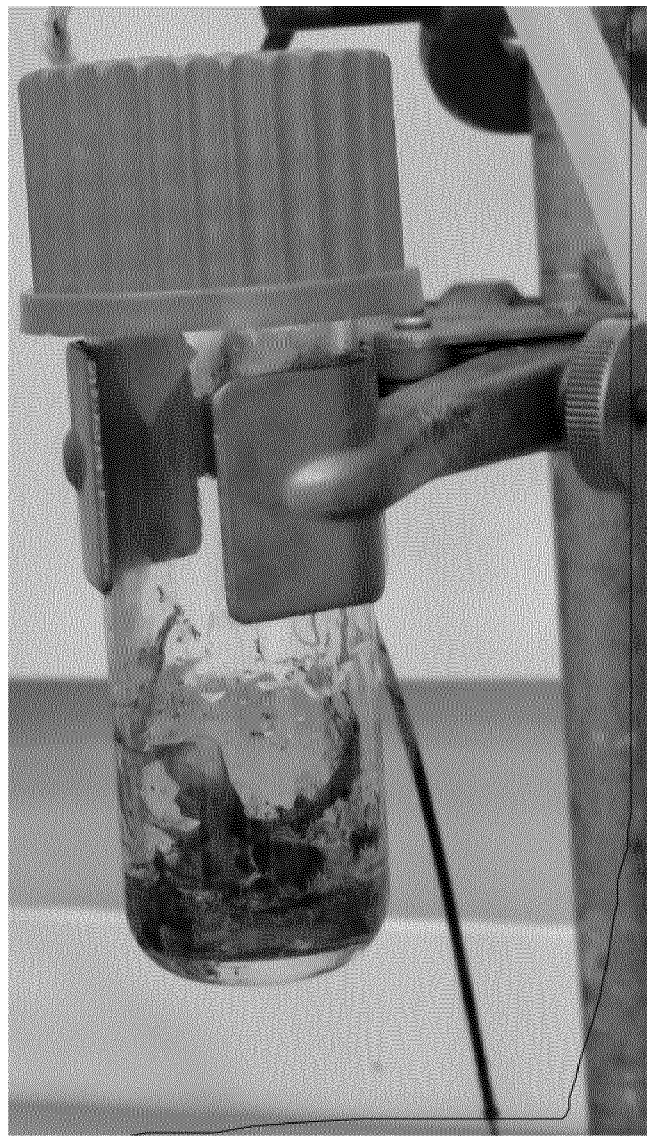
FIG. 2 shows the product of melting at 280°]C. a sample of HDPE and PP under air atmosphere.

The same procedure as in Example 2 is repeated but without replacing the air contained in the test tube by inert atmosphere. The $O_2$ content in the gas phase is estimated at 21 to 22 vol %. The tube is heated externally up to 280° C. The plastic does not melt but carbonizes as seen in FIG. 2.

EXAMPLE 4 to 7

2 g of HDPE, 0.5 g of PP and 25 mg of PS small pieces of different commercial plastic items and 10 g of solvent were introduced in a glass test tube of 30 ml equipped with a magnetic agitator at room temperature. The glass tubes were then flushed with argon to remove most of the O2 atmosphere and the tubes were sealed with a conventional stopper. The tubes were heated to 200° C. in an oil bath in four steps (120, 150, 180 and 200° C., respectively) under agitation and the mixture was observed.

4 different tubes were prepared with the following results:

|  | Example | | | |
| --- | --- | --- | --- | --- |
|  | 4 | 5 | 6 | 7 |
| Solvent | Octane | Docosane | Hexatriacontane | 40% Octane + 40% Octadecane + 20% Hexa-triacontane |
| Boiling point of the solvent | 125° C. | 369° C. | 265° C. under 1 mmHg | Not determined |
| Melting point of the solvent | Not determined | 45° C. | 76° C. | Not determined |
| Room temperature | Liquid solvent + solid plastic | Solid solvent and plastic | Solid solvent and plastic | Liquid + solid solvent and solid plastic |
| 120° C. | Solvent: liquid Plastic: solid | Solvent: liquid Plastic: solid | Solvent: liquid Plastic: solid | Solvent: liquid Plastic: solid |
| 150° C. | Solvent: liquid Plastic partially solubilized | Solvent: liquid Plastic partially solubilized | Solvent: liquid Plastic: solid | Solvent: liquid Plastic: solid |
| 180° C. | Not totally soluble | Soluble | Not totally soluble | Soluble |
| 200° C. | Soluble | Soluble | Soluble | Soluble |

Should the disclosure of any patents, patent applications, and publications which are incorporated herein by reference conflict with the description of the present application to the extent that it may render a term unclear, the present description shall take precedence.

The invention claimed is:

1. Process for the treatment of a composition comprising thermoplastics, the process comprising the steps of
    a) introducing the composition comprising thermoplastics into a reactor under reduction of oxygen content of the atmosphere, wherein the oxygen content is reduced to below 10 vol % of gas phase,
    b) heating the composition to a temperature in the range of 150° C. to 450° C. in the presence of a solvent, wherein the solvent has a boiling point of between 50° C. and 150° C. and wherein the amount of solvent is 0.1 kg to 10 kg per kg of thermoplastics, to obtain a drop in viscosity below $10^4$ mPas of at least 50% by weight of the thermoplastics, based on the total content of the thermoplastics,
    c) separating solid and/or gaseous fractions of the composition at the surface of the mixture and/or the bottom of the reactor, and
    d) recovering liquefied thermoplastics from the reactor, wherein the process steps a) to c) are conducted in one reactor.

2. Process according to claim 1, wherein the process steps a) to c) are conducted continuously.

3. Process according to claim 1, wherein the solvent used in step b) is an aliphatic hydrocarbon.

4. Process according to claim 1, wherein the solvent used in step b) is a $C_6$ to $C_8$ alkane or a mixture of $C_6$ to $C_8$ alkanes.

5. Process according to claim 1, wherein the solvent forms an azeotropic mixture with water.

6. Process according to claim 1, wherein in step b) the composition is heated in the presence of the solvent to a temperature in the range of above 250° C. to 400° C.

7. Process according to claim 1, wherein the composition comprises at least 80% polyethylene, polypropylene and polystyrene as thermoplastics.

8. Process according to claim 1, wherein steps a) to d) are followed by a step e) of cracking the liquefied thermoplastics.

9. Process according to claim 8, wherein the cracking is thermal or catalytic cracking.

10. Process according to claim 1, wherein the composition comprises waste plastic.

11. Process according to claim 1, wherein steps a) to d) are preceded by a step of reduction of the particle size of the thermoplastics.

12. Process according to claim 2, wherein the process steps a) to c) are conducted simultaneously in the reactor.

* * * * *